United States Patent
LePlang et al.

[11] Patent Number: 5,141,635
[45] Date of Patent: Aug. 25, 1992

[54] FLUID DISTRIBUTOR AND DEVICE FOR TREATING A FLUID SUCH AS A CHROMATOGRAPH EQUIPPED WITH SAID DISTRIBUTOR

[75] Inventors: Michel LePlang, Villiers Sur Marne; Daniel Chabrol, Villemomble, both of France

[73] Assignee: Biopass, France

[21] Appl. No.: 651,343

[22] PCT Filed: May 27, 1989

[86] PCT No.: PCT/EP89/00593
§ 371 Date: Feb. 4, 1991
§ 102(e) Date: Feb. 4, 1991

[87] PCT Pub. No.: WO89/11901
PCT Pub. Date: Dec. 14, 1989

[30] Foreign Application Priority Data
Jun. 3, 1988 [FR] France .................. 88 07413

[51] Int. Cl.⁵ .............................. B01D 15/08
[52] U.S. Cl. ...................... 210/198.2; 210/656; 55/386
[58] Field of Search .......... 210/635, 656, 659, 198.2, 210/198.3, 456; 55/67, 386

[56] References Cited
U.S. PATENT DOCUMENTS

| | | | |
|---|---|---|---|
| 3,966,609 | 6/1976 | Godbille et al. | 210/198.2 |
| 4,582,608 | 4/1986 | Ritacco | 210/656 |
| 4,597,866 | 7/1986 | Couillard | 210/198.2 |
| 4,636,315 | 1/1987 | Allen | 210/198.2 |
| 4,743,373 | 10/1988 | Rai | 210/198.3 |
| 4,769,141 | 9/1988 | Couillard | 210/198.2 |
| 4,797,209 | 1/1989 | Jackson | 210/198.2 |
| 4,891,133 | 1/1990 | Colvin | 210/198.2 |
| 4,894,152 | 1/1990 | Colvin | 210/198.2 |
| 4,927,531 | 5/1990 | Sakamoto | 210/198.2 |

FOREIGN PATENT DOCUMENTS

| | | | |
|---|---|---|---|
| 0108242 | 5/1984 | European Pat. Off. | 210/198.2 |
| 2085614A | 4/1982 | United Kingdom | 210/198.2 |

Primary Examiner—Ernest G. Therkorn
Attorney, Agent, or Firm—Bacon & Thomas

[57] ABSTRACT

The invention relates to a fluid distributor, particularly for a chromatography apparatus of large diameter in relation to its height.

The distributor (2) comprises a separator (20) consisting of a disc of porous material, and a distribution plate (21) comprising, on its face in contact with the separator, annular channels (29 to 33) connected to a feed or discharge line by conduits (34 to 43) whose dimensions are calculated in order to introduce, in operation, a pressure drop which is inversely proportional to the area of the corresponding channel, measured on its surface of the separator.

11 Claims, 3 Drawing Sheets

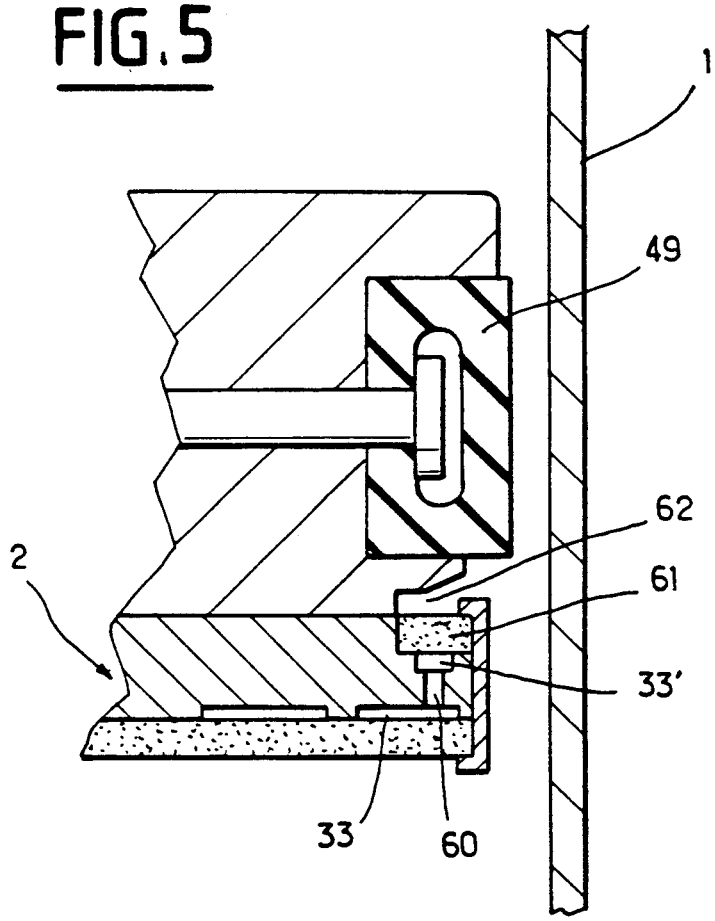

FLUID DISTRIBUTOR AND DEVICE FOR TREATING A FLUID SUCH AS A CHROMATOGRAPH EQUIPPED WITH SAID DISTRIBUTOR

The present invention relates to a fluid distributor, intended to ensure a uniform distribution of pressures and flow rates in the cross-section of a stream of the said fluid, as well as to a device for treating a fluid, equipped with a distributor of this kind, and employed particularly in chromatography.

Chromatographic techniques are at present enjoying an increasing success, in particular those according to which a liquid is passed through a mass of beads of porous material, in order to separate the components present in this liquid. Among the most important applications there may be mentioned blood treatment, as well as many processes in the field of biotechnologies. Progress in the methods leads to the use of chromatography columns of increasing size, capable of reaching a diameter of the order of 1 meter, and a height of 0.9 meter. The material required for chromatography, which, in the case of low pressures, is made up of beads 20 to 200 micrometers in diameter, made of spongy gelatine, and, in the case of high pressures, of silica particles of similar shapes and dimensions, is very costly. It must therefore be employed as efficiently as possible and this means that the distribution of the stream of fluid through these large columns must be as uniform as possible.

Chromatography columns usually consist of a vertical cylindrical enclosure, generally made of glass, closed at its lower and upper ends by a distributor comprising a separator consisting of a plate of porous material with open porosity, for example sintered polypropylene, and a distribution plate which rests on the separator and comprises at least one channel on its side facing the separator, this plate being crossed by at least one conduit connecting the said channel, or the said channels, to a single feed channel situated on the opposite side.

In the most commonplace embodiment, such as described in patent GB-A-2 085 614, the conduit is central, and the channels go out diverging from the centre towards the periphery, branching, so as to offer, substantially over the whole surface of the plate, an approximately constant ratio between the areas devoted to the flow of fluid and those used to support the separator. The depth or the width of the grooves must increase on approaching the centre, so as to ensure a uniform flow of liquid. As a result of this, production of such components, which is usually performed by moulding, is very costly. In fact, the machining of a suitable mould in a highly resistant steel is difficult to obtain and requires much time and care. An imperfect mould results in defects in the plate, which can give rise to cleaning difficulties.

The objective of the present invention is to provide a distributor in which the production of the distribution plate is much simpler and whose cost of manufacture is much more reasonable.

Another objective of the invention is to provide a device for treating fluid, such as a chromatograph, in which the disassembly operations and adjustments are easy and quick.

To obtain this result, the invention provides a fluid distributor intended to ensure a uniform distribution of the pressures and flow rates over the cross section of a stream of the said fluid, this distributor comprising a separator (20) consisting of a plate of porous material with open porosity and a circular distribution plate (21) bearing on the separator comprising at least one open channel on its side facing the separator, and being crossed by at least one conduit connecting the said at least one channel to a single feed or discharge line situated on the opposite edge, said at least one conduit (34–43) connecting the said at least one channel to the feed or discharge line introducing, in operation, a pressure drop between the said line and the corresponding channel, which is inversely proportional to the area of the corresponding channel, measured over the surface of the separator, characterized in that said channels are circular and concentric, said at least one conduit connecting said channels to the feed or discharge line comprising star-shaped grooves (34, 36, 38, 40, 42) hollowed out in the side of the distribution plate which faces away from the separator, these grooves being covered by a support plate (5) in contact with the distribution plate, said at least one conduit additionally comprising passages (35, 37, 39, 41, 43) perpendicular to the distribution plate, opening into a groove on the one side and into a channel on the other side.

Avantageously, the cross-section of these passages is smaller than the grooves into which they open out.

Here again, it can be seen that a shape which is simple and easy to obtain is involved. It will be noted that it is not necessary for the depth of the grooves to vary as they move away from the centre, or even to vary from one groove to another, since the pressure drop is obtained chiefly with the aid of the passages which pass through the plate.

According to an advantageous form, the passages are provided with interchangeable nozzles to permit the pressure drop in the corresponding conduit to be adjusted. Using the same single plate it is thus possible to allow for different viscosities of the fluids to be treated.

The areas of the channels of the distribution plate are advantageously equal to each other and the pressure drops introduced by the conduits are equal to each other.

To obtain a device for treating a fluid, such as a device for treatment by chromatography, a cylindrical enclosure is advantageously provided, which is closed at its ends by two distributors of the above type, these distributors being arranged with their separation facing.

To make it easier to dismantle and adjust the dimensions of an enclosure of this kind, it has been found advantageous for the distributor to be fastened to a support plate provided with an inflatable seal ensuring sealing to the side wall of the enclosure.

In the devices of the prior art, the sealing between each distributor and the side wall of the enclosure is obtained by squashing an O ring. A solution of this kind is difficult to apply in the case of large diameters because considerable forces must then be provided to squash the O ring in a suitable manner and/or very high accuracy must be provided in the diameter of the distributor and of the inner wall of the enclosure. Moreover, even a small obliqueness of the plane of the distributor relative to the axis of the enclosure can make the sealing faulty. The use of a suitable seal does not involve large forces. In addition, its great distortion latitude permits much greater dimensional tolerances.

In order to obtain an inflatable clamping of the mass of chromatographic medium which fills the space included between the two separators, in a chromatograph of large diameter arranged vertically, it is advantageously provided for the upper distributors to be fastened to a plate which can be carried by a central supporting rod, with a clearance which corresponds to the compressibility of the mass of chromatograph medium, and vertical tamping rods arranged near the periphery of this plate provide the desired and uniform clamping of the said mass.

BRIEF DESCRIPTION OF THE DRAWINGS

The invention will now be described in a more detailed manner with the aid of a practical example, illustrated with the aid of the drawings, among which:

FIG. 5 represents a preferred embodiment of the present invention.

DESCRIPTION OF THE PREFERRED EMBODIMENTS

The chromatograph described in the figures is an apparatus of large size, with a diameter of approximatively 450 mm, this size being given by way of example, and of comparable height. Such equipment is employed for separating a component from a liquid, for example the separation of the serum present in blood. The low value of the height/diameter ratio obviously demands a very good distribution of the liquid flow over the whole cross-section.

Figure 1:
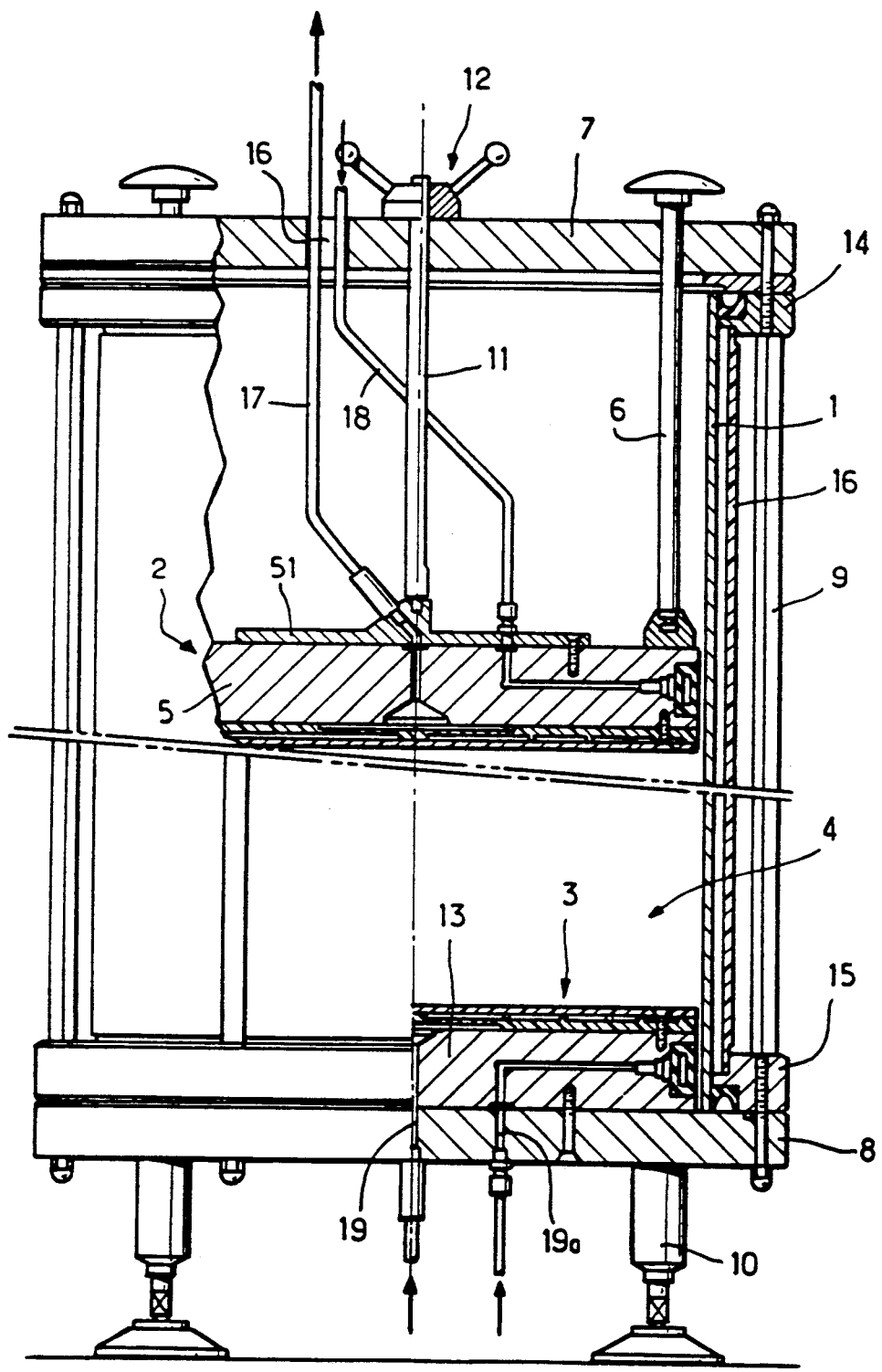
FIG. 1 is a partially sectioned general view of a chromatography column in accordance with the invention.

The chromatograph, which can be seen as a whole in FIG. 1, comprises a cylindrical tube of revolution 1, arranged vertically, an upper distributor 2, and a lower distributor 3, with the volume 4 defined by these two distributors forming the working chamber, which is filled with a mass of beads of porous gelatine, which forms the separating material in this case.

The upper distributor 2 is fastened to a support plate 5 and forms with it a plunger which can move inside the tube 1, and this allows its position to be adapted to the exact volume of the beads placed in the volume 4. Tamping rods 6, distributed uniformly along the periphery of the support plate 5, allow a suitable pressure to be exerted on the mass of beads. These tamping rods bear, by virtue of a threading, on an upper end plate 7 mounted on top of the tube 1. The end plate 7 is itself connected to a lower end plate 8 by a series of uniformly distributed tie rods 9 arranged outside the tube 1. The lower end plate 8 carries feet 10, which support the whole apparatus. When the apparatus is dismantled and reassembled, the weight and the large size of the plunger consisting of the upper distributor 2 and its support plate make it tricky to handle. To make handling easier, the plate 5 is connected to the upper end plate 7 by a supporting rod 11, situated in its central part, and equipped with a means for manual lifting 12, carried by the plate 7. A safety device, not shown, prevents the rod 11 and the device 12 from being subjected to excessive forces when the tamping rods 6 are tightened.

The lower distributor 3 is provided with a support plate 13, identical with the support plate 5 of the upper distributor. This support plate rests on the lower end plate 8.

Upper 14 and lower 15 positioning rings, through which the tie rods 9 pass, hold the glass tube 1 in position relative to the end plates 7 and 8. Furthermore, they support a tube 16 made of transparent plastic (methyl methacrylate) concentric with the glass tube 1, which is slightly larger in diameter and which serves both as mechanical protection and, if appropriate, as thermal protection, it being possible, if appropriate, for a liquid which keeps the temperature constant to flow through the volume between the two tubes.

Passing through the upper end plate 7 is a large orifice 16 providing a passage, on the one hand, for a flexible tube 17 for discharging the treated liquid and, on the other hand, a flexible tube 18 for feeding compressed air to the seals, as will be seen later. The orifice 16 is also used to open the upper face of the support plate 5 to the atmosphere.

The end plate 8 has a passage 19 for delivering the fluid to be treated and a passage 19a for delivering compressed air for the seals. It will be noted that there is nothing to prevent a reverse direction of travel, that is to say that the conduit 17 can be a delivery conduit and the passage 19 a passage for discharging the fluid.

Cap seals (not shown) are obviously provided in the appropriate places.

Figure 2:
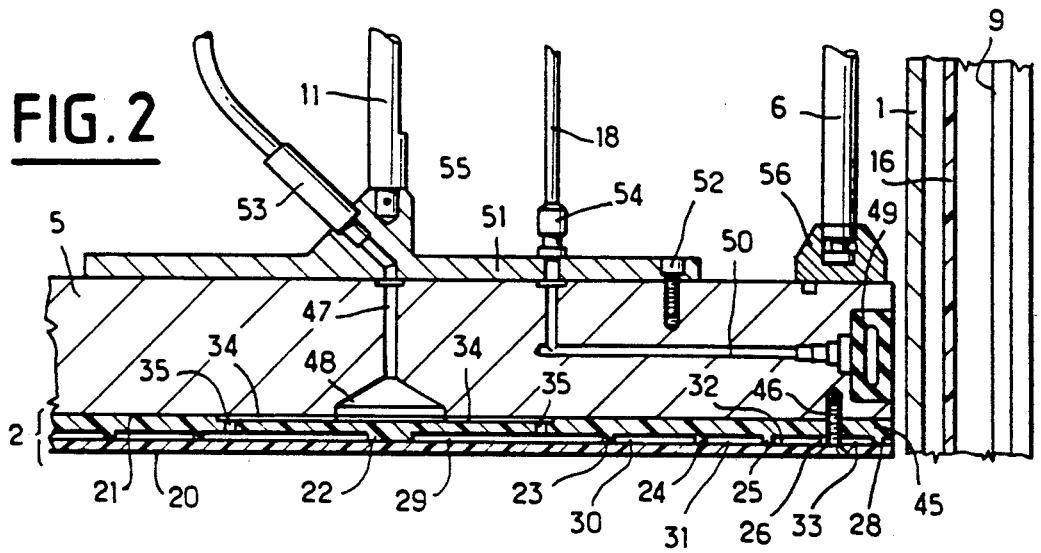
FIG. 2 is a partial section, on a larger scale, of a distributor according to the invention.

FIG. 2 is a partial, more detailed, cross-section of a preferred embodiment of the upper distributor 2 of its support plate 5 and of the neighbouring components.

Figure 4:
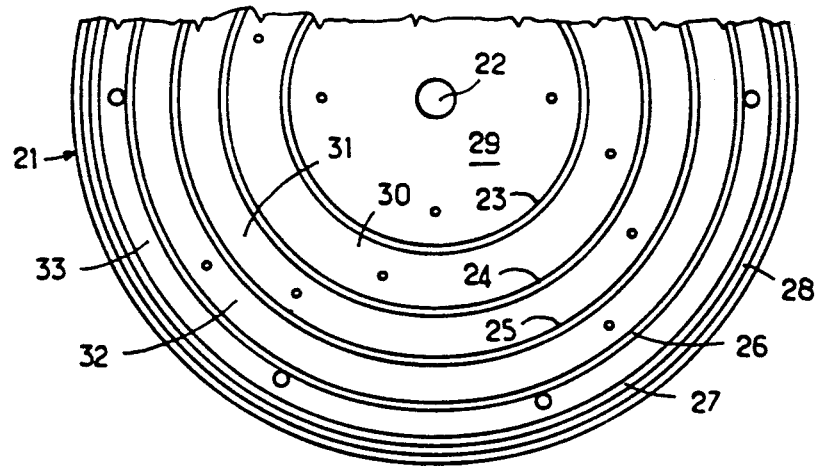

The distributor 2 is made up of a separator 20 consisting of a simple circular plate of sintered polypropylene and of a distribution plate 21 consisting of a plate of rigid plastic whose lower face, that is to say that which is in contact with the separator 20, is shown in FIG. 4. This lower face comprises projecting parts, all in the same plane, which provide the contact with the separator 20, and hollow parts, also all in the same plane. The projecting parts comprise a circular central projection 22 and a series of concentric annular ribs 23, 24, 25 and 26, as well as an edge rib 27. The circular central projection 22, of small diameter, occupies approximately 1/1000 of the total surface area of the distribution plate. The circular ribs 23 to 26 are small in width and, as a group, they make up approximately 1/100 of the total surface area of the distribution plate. The edge rib 27 is slightly wider and on its inner edge it is associated with a seal 28.

The projection 22 and the ribs 23 to 27 define between them channels 29, 30, 31, 32 and 33 which are limited in their upper part by the body of the distribution plate and, in their lower part, by the separator 20. In radial section, as shown in FIG. 2, their cross-section is rectangular, with a constant height, and a width which depends on the relative position of the projection 22 and of the various ribs. The position of these ribs and the radius of the projection 22 are calculated so that the area of the various channels, measured in the plane of contact between the separator 20 and the distribution plate 21 should be the same from one channel to another. This requires the difference (Re2−Ri2) to be constant for each of the channels, Re and Ri denoting the radius of the inner edge and of the outer edge of the channel, measured from the axis of the distribution plate.

The calculation of the position of the central projection and of the various ribs does not present any difficulty from the standpoint of mathematics. The number of ribs is determined by mechanical considerations and they must, in fact, be sufficient in number to oppose any distortion of the separator 20.

Figure 3:
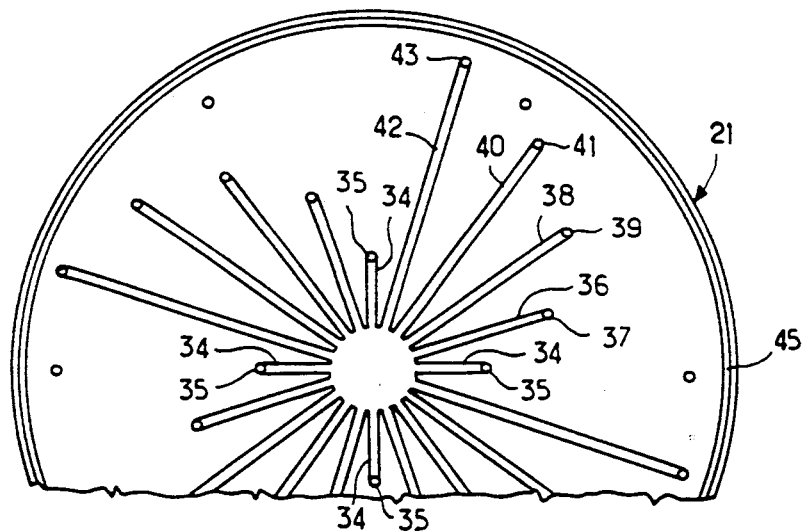
FIGS. 3 and 4 are partial views from above and from below respectively, of the distribution plate of the distributor of FIG. 2.

The upper face of the distribution plate 21 is shown in FIG. 3. It is planar as a whole, but has a series of grooves arranged star-fashion, these grooves being identical in cross-section, but of variable lengths. Four first grooves 34 run from the central region as far as a transverse passage 35 which passes through the plate and open into the bottom of the first channel 29 starting from the centre. Four other grooves 36 are likewise connected to passages 37 opening into the bottom of the second channel 30. Similar grooves 38, 40 and 42, of increasing lengths, are similarly connected to passages 39, 41 and 43 opening into the following channels 31, 32 and 33 respectively. Each group of four ribs of the same length forms a four-pointed star, so that the passages opening into the bottom of the successive channels are distributed uniformly.

The passages 35, 37, 39, 41 and 43 are not identical with each other. Their cross-section is calculated so that the pressure drop introduced between the central dish 44 and the corresponding channel 29 to 33 is the same for all the channels. Uniform pressure and flow rate conditions are thus obtained for all the channels, that is to say substantially for the whole surface of the separator. Very small differences are evened out by virtue of the permeability of the separator, which acts as a diffuser. The characteristic section of the channels 29 to 33 is sufficiently large not to perturb this uniformity. It should be remembered, in fact, that the flow velocities in a chromatography apparatus are very low.

In the example described, the passages 35, 37, 41 and 43 are simply drilled through the distribution plate 21. It would also be possible to provide calibrated constrictions fitted into pre-drilled orifices. This more complicated alternative form would make it possible to modify the pressure drops as a function of the working conditions in order always to obtain an optimum equalization of the pressures and flow rates in the separator and hence in the working volume 4.

The various grooves converge towards the centre into a central distribution zone 44 forming a kind of dish. The central projection 22 provided on the opposite face serves to prevent excessive mechanical weakening of this zone.

Near its peripheral edge, the upper face of the distribution plate 21 is provided with a ring seal 45, similar to the seal 28. Screws 46 pass both through the separator 20 and the distribution plate 21 and are fastened into the support plate 5, which is appreciably thicker. This support plate, which is cylindrical, with a radius substantially equal to that of the distributor 2, is in contact with the upper face of the distribution plate 21 over the part of its surface which is not occupied by the grooves or by the central dish 44. In its central part, the support plate 5 has a fluid channel 47, arranged axially and opening in the lower part into a distribution channel 48 which faces the dish 44.

On its peripheral edges, the plate 5 has a circular groove housing a seal 39 consisting of an annular chamber which can be inflated with compressed air, the compressed air being delivered by means of a conduit 50 arranged within the thickness of the plate 5. The dimensions of the seal 49 are calculated so that it can, in any event, ensure a proper sealing of the inner volume 4 relative to the exterior, even if the plate 5 were to be slightly oblique relative to the axis. In FIG. 2, the seal 49 is shown in the deflated state. A connecting and anchoring component 51 is fastened by means of screws 52 to the upper face of the plate 5. This component 51 carries an adaptor 53 for the flexible tube 17 for discharging the liquid, this adaptor 53 being, of course, connected to the axial passage 47. It also carries an adaptor 54 for the flexible conduit 18, which is used to feed compressed air to the inflatable seal 49 by means of the passage 50. Furthermore, it carries the means for anchoring 55 the supporting rod 11. The clearance needed to prevent excessive forces on the rod 11 can be contained in the anchoring device 55, as it can be in the actuating means 12, shown in FIG. 1.

56 shows a component at the end of the tamping rod 6 fitted onto the latter with a swivel joint and having a surface bearing on the plate 5.

For the sake of simplicity, the lower distributor 3 and its support plate 13 are absolutely identical with the upper distributor 2 and with its support plate 5. They are merely inverted, the distributor 3 being above the support plate 13 and, in the distributor 3, the separator being above the distribution plate. There is therefore no need to describe them in detail.

The device just described is particularly simple, both in its construction and in its operation, particularly insofar as the dismantling and the reassembly are concerned.

FIG. 5 represents a detail of preferred embodiment of the present invention. It is to note that in the above mentioned embodiments, there is a "dead zone" delimited by the lower part of the inflatable seal 49, the glass tube 1 and the movable plunger, said "dead zone" exhibits the drawback of never being drained by the liquid flow.

It is particularly a nuisance when several different products are chromatographed one after the other. As a matter of fact, the cleaning between two series of different products is not efficient in said "dead zone". Thus, in the embodiment of FIG. 5, holes 60 are made which communicate with the peripheral channel 33 of the distributor and emerge via filter 61 on the lateral wall of the plunger by means of a peripheral rib 62 placed under the inflatable seal 49, thus ensuring a lateral distribution of the fluid in said "dead zone", said holes being distributed on the whole periphery of the distributor. The advantage resulting will more significant if said lateral distribution is very close to the inflatable seal 49. By way of example, the hole diameter can be about 1 mm, but shall not cause significant head losses. On the other hand, according to the invention, the total surface of both channels 33 and 33' (33' being the channel emerging on the peripherical rib via filter 61) is equal to the surface of the other channels 29, 30, 31, 32.

We claim:

1. In a fluid distributor intended to ensure a uniform distribution of the pressures and flow rates over the cross section of a stream of the said fluid, this distributor comprising a separator (20) consisting of a plate of porous material with open porosity and a circular distribution plate (21) bearing on the separator comprising at least one open channel on its side facing the separator, and being crossed by at least one conduit connecting the said at least one channel to a single feed or discharge line situated on the opposite edge, said at least one conduit (34–43) connecting the said at least one channel to the feed or discharge line introducing, in operation, a pressure drop between the said line and the corresponding channel, which is inversely proportional to the area of the corresponding channel, measured over the surface of the separator, the improvement wherein said channels are circular and concentric, said at least one conduit connecting said channels to the feed or discharge line comprises star-shaped grooves (34, 36, 38, 40, 42) hollowed out in the side of the distribution plate which faces away from the separator, these grooves being covered by a support plate (5) in contact with the distribution plate, said at least one conduit additionally comprising passages (35, 37, 39, 41, 43) perpendicular to the distribution plate, opening into a groove on the one side and into a channel on the other side.

2. Distributor according to claim 1, wherein said passages have a cross-section which is smaller than the grooves into which they open out.

3. Distribution according to claim 2, wherein said passages are provided with interchangeable nozzles to permit the pressure drop in the corresponding conduit to be adjusted.

4. Distributor according to claim 1 wherein said passages are provided with interchangeable nozzles to permit the pressure drop in the corresponding conduit to be adjusted.

5. Distributor according to claim 1, wherein the areas of the channels (29 to 33) are equal to each other and the pressure drops introduced by the conduits are equal to each other.

6. Device for treating a fluid, comprising a cylindrical enclosure (1) closed by two distributors (2, 3), wherein the distributors are in accordance with one of claims 1, 2, 3, or 4 and are arranged with their separators facing each other.

7. Device according to claim 6, wherein in order to facilitate the dismantling and the adjustment of the dimensions of the enclosure, each distributor is fastened to a support plate (3) provided with an inflatable seal (49) ensuring sealing to the side wall of the enclosure.

8. Device according to claim 7 wherein holes (60) are made which communicate with the peripheral channel (33) of the distributor (2) and emerge on the lateral wall of the movable plunger under the inflatable seal (49), said holes being distributed on the whole periphery of the distributor.

9. Device according to claim 5, said device forming a chromatograph arranged vertically, in which the volume (4) included between the two separators contains a mass of chromatography medium, wherein the upper distributor is fastened to a plate (5) which is carried by means of a central supporting rod (11) with a clearance which corresponds to the compressibilty of the mass of chromatography medium, and vertical tamping rods (6) arranged near the periphery of this plate ensure an appropriate clamping of the said mass.

10. Device according to claim 6, wherein, in order to facilitate the dismantling and the adjustment of the dimensions of the enclosure;

said device forming a chromatograph arranged vertically in which the volume (4) included between the two separators contains a mass of chromatography medium, wherein the upper distributor is fastened to a plate (5) which is carried by means of a central supporting rod (11) with a clearance which corresponds to the compressibility of the mass of chromatography medium, and vertical tamping rods (6) arranged near the periphery of this plate ensure an appropriate clamping of the said mass.

11. Device according to claim 10, wherein, holes (6) are made which communicate with the peripheral channel (33) of the distributor (2) and emerge on the lateral wall of the movable plunger under the inflatable seal (49), said holes being distributed on the whole periphery of the distributor.

* * * * *